(12) United States Patent
Wu et al.

(10) Patent No.: US 9,790,199 B1
(45) Date of Patent: Oct. 17, 2017

(54) SULFOXIDE COMPOUND AND METHOD OF PRODUCING BENZOTHIOPHENE DERIVATIVES USING THE SAME

(71) Applicant: NATIONAL SUN YAT-SEN UNIVERSITY, Kaohsiung (TW)

(72) Inventors: Ming-Jung Wu, Kaohsiung (TW); Shih-Ming Wen, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 15/455,117

(22) Filed: Mar. 9, 2017

(30) Foreign Application Priority Data

Dec. 1, 2016 (TW) .............................. 105139744 A

(51) Int. Cl.
*C07D 409/00* (2006.01)
*C07D 333/56* (2006.01)
*C07C 317/22* (2006.01)

(52) U.S. Cl.
CPC .......... *C07D 333/56* (2013.01); *C07C 317/22* (2013.01)

(58) Field of Classification Search
CPC .................................................. C07D 333/56
USPC ....................................................... 546/202
See application file for complete search history.

(56) References Cited

U.S. PATENT DOCUMENTS

| 4,133,814 A | 1/1979 | Jones et al. |
| 4,380,635 A | 4/1983 | Peters |
| 4,418,068 A | 11/1983 | Jones |
| 6,458,811 B1 | 10/2002 | Arbuthnot et al. |

OTHER PUBLICATIONS

Sousa, European Journal of Organic Chemistry, 2014(9), 1855-1859; 2014.*
Lin et al. Chem. Eur. J. 2013, 19, 2578-2581.*

* cited by examiner

*Primary Examiner* — Nizal Chandrakumar
(74) *Attorney, Agent, or Firm* — CKC & Partners Co., Ltd.

(57) ABSTRACT

A sulfoxide compound and method of producing benzothiophene derivatives using the same are provided. The sulfoxide compound is represented by formula (I), wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain; and X is halogen atom. The sulfoxide compound reacts with alkynyl compound, and then the synthesis efficiency of benzothiophene derivatives can be effectively increased.

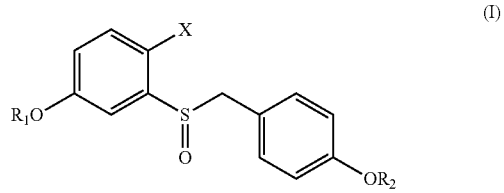

7 Claims, No Drawings

SULFOXIDE COMPOUND AND METHOD OF PRODUCING BENZOTHIOPHENE DERIVATIVES USING THE SAME

RELATED APPLICATION

This application claims priority to Taiwan Application Serial Number 105139744, filed Dec. 1, 2016, which is herein incorporated by reference.

BACKGROUND

Field of Invention

The present invention relates to sulfoxide compound and its application. More particularly, the present invention relates to method of producing benzothiophene derivatives from a sulfoxide compound having specific structure.

Description of Related Art

Benzothiophene derivatives are aromatic heterocyclic compounds, which are important intermediates of various pharmaceutical synthesis processes.

For example, raloxifene, which has been reported as one of unique selective estrogen receptor modulators (SERMs), is a benzothiophene derivative. SERMs show the function similar to estrogen on metabolism of skeleton and cholesterol. Moreover, SERMs also do antiestrogenic effect on breasts and endometrial hyperplasia. It is known that the mechanism of breast cancer arisen by estrogen is the combination of estrogen and receptor resulting in proliferation and differentiation of breast cancer cells. SERMs can make competition against the activation of estrogen receptor in breast cells. The main interaction between raloxifene, tissues and cells is first forming a complex by binding raloxifene to estrogen receptor, then the complex binds to various genes to initiate or inhibit the expression of genes. Thus, raloxifene and Tamoxifen, the first generation SERMs, can both reduce the incidence of invasive breast cancer. In addition, raloxifene can replace estrogen to increase bone mass density (BMD), improve osteoporosis, and lower concentrations of cholesterol and low-density lipoprotein in the blood. Therefore, processes of synthesizing benzothiophene derivatives have recently attracted great attention.

Some traditional methods of producing benzothiophene derivatives are described in U.S. Pat. No. 6,458,811, U.S. Pat. No. 4,133,814, U.S. Pat. No. 4,418,068 and U.S. Pat. No. 4,380,635, as shown in Reaction Scheme 1, all of which is incorporated herein by reference. Briefly speaking, in the traditional methods, 3-alkoxybenzenethiol [for example, the compound of formula (i)] and phenacyl bromide [for example, the compound of formula (ii)] firstly react in the presence of strong base to form aryl phenacylsulfide [for example, the compound of formula (iii)]. Next, aryl phenacylsulfide is heated to perform an intramolecular cyclization step in the presence of polyphosphoric acid (PPA), for forming 2-phenyl benzothiophene [for example, the compound of formula (iv)]. And then, the 2-phenyl benzothiophene and benzoyl chloride compound having different substituent groups [such as the compound of formula (v)] react to benzothiophene derivatives with benzoyl group [for example, the compound of formula (vi)] such as raloxifene of formula (vii) in Friedel-Crafts reaction.

However, in the traditional methods, the intramolecular cyclization tends to form two isomers of the benzothiophene derivatives, resulting in the decreased yield of the intermediates. Furthermore, the steps of the traditional methods are so complicated, which lead to poor synthesis efficiency.

Accordingly, it is necessary to provide a method of producing benzothiophene derivatives to prevent complicated reaction steps from decreasing synthesis efficiency of benzothiophene derivatives.

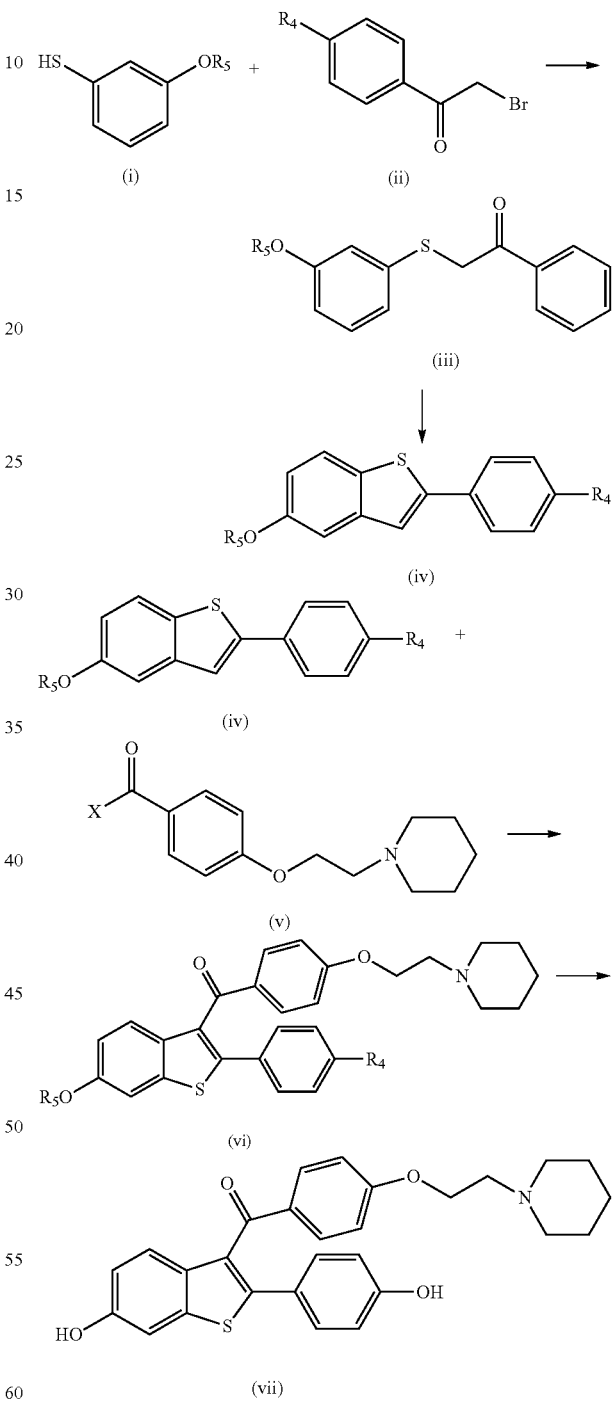

[Reaction Scheme 1]

SUMMARY

In one aspect, the invention provides a sulfoxide compound.

In another aspect, the invention is directed to a method of producing a benzothiophene derivative by reacting the aforementioned sulfoxide compound and an alkynyl compound for a specific period of time, thereby increasing the production efficiency.

In yet another aspect, the invention provides a benzothiophene derivative, which is produced by the aforementioned method.

According to the aforementioned aspect of the present invention, the invention provides a sulfoxide compound of formula (I), wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain; and X is halogen atom.

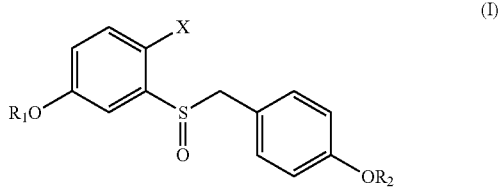

(I)

According to another aspect of the present invention, providing a method of producing a benzothiophene derivative. Perform a reaction between a sulfoxide compound of formula (I) and an alkynyl compound of formula (II) to produce the benzothiophene derivative. In the formula (II), wherein A is hydrogen atom or silyl group and $R_4$ is benzoyl group; alkyl, acyl or silyl group of $C_1$-$C_6$ straight chain or branched chain; or alkenyl group of $C_3$-$C_6$ straight chain or branched chain. In the formula (III), wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain, and $R_3$ is hydrogen atom or (1-piperidinyl)-($C_1$-$C_4$)alkyl group.

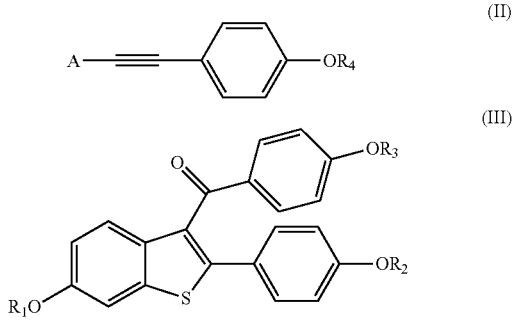

(II)

(III)

According to further another aspect of the present invention, providing a benzothiophene derivative, which is produced by the method according to the aforementioned aspect.

These and other features, aspects, and advantages of the present invention will become better understood with reference to the following description and appended claims.

It is to be understood that both the foregoing general description and the following detailed description are by examples, and are intended to provide further explanation of the invention as claimed.

DETAILED DESCRIPTION

General terms used in the description of compounds, methods, and formulations herein bear their usual meanings.

For example, "$C_1$-$C_4$ alkyl group" refers to methyl group, ethyl group, propyl group, iso-propyl group, cyclopropyl group, n-butyl group, s-butyl group, t-butyl group, and cyclobutyl group. The term "$C_1$-$C_6$ alkyl group" encompasses those listed for $C_1$-$C_4$ alkyl group in addition to monovalent, straight, branched, or cyclic alphatic chains of 5 or 6 carbon atoms including pentyl group, cyclopentyl group, hexyl group, 2-methyl pentyl group, cyclohexyl group, and the like. The term "$C_1$-$C_4$ alkoxy group" refers to methoxy group, ethoxy group, n-propoxy group, iso-propoxy group, cyclopopoxy group, n-butoxy group, s-butoxy group, t-butoxy group, and cyclobutoxy group. The term "$C_1$-$C_6$ alkoxy group" encompasses those listed for $C_1$-$C_4$ alkoxy group in addition to straight, branched, or cyclic aliphatic chains of 5 or 6 carbon atoms which are attached through a monovalent oxygen atom and include but are not limited to, pentoxy group, cyclopentoxy group, hexoxy group, 2-methylpentoxy group, cyclohexoxy group, and the like.

The term "halide" refers to chloride, bromide, or iodide.

The term "substituted phenyl group" refers to a phenyl group having one to three substituents selected from the group consisting of $C_1$-$C_6$ alkyl group, $C_1$-$C_4$ alkoxy group, hydroxy group, nitro group, chloro, or tri(chloro or fluoro) methyl group.

The term "aryl group" refers to a carboxylic aromatic system containing one, two, or three rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The term "aryl group" embraces aromatic radicals such as phenyl group, naphthyl group, tetrahydronaphthyl group, indanyl group, biphenyl group, benzo[b][1,4]oxazin-3(4H)-onyl, 2,3-dihydro-1H-indenyl group, and 1,2,3,4-tetrahydronaphthalenyl group.

The term "heteroaryl group" means an aromatic carbocyclic system containing one, two, three, or four heteroatoms selected independently from oxygen, nitrogen, and sulfur and having one, two, or three rings wherein such rings may be fused, wherein fused is defined above. The term "heteroaryl group" includes but is not limited to furyl group, thienyl group, oxazolyl group, thiazolyl group, imidazolyl group, pyrazolyl group, triazolyl group, tetrazolyl group, isoxazolyl group, isothiazolyl group, oxadiazolyl group, thiadiazolyl group, pyridinyl group, pyridiazinyl group, pyrimidinyl group, pyrazinyl group, pyridin-2(1H)-onyl group, pyridazin-2(1H)-onyl group, pyrimidin-2(1H)onyl group, pyrazin-2(1H)-onyl group, imidazo[1,2-a]pyridinyl group, pyrazolo[1,5-a]pyridinyl group, 5,6,7,8-tetrahydroisoquinolinyl group, 5,6,7,8-tetrahydroquinolinyl group, 6,7-dihydro-5H-cyclopenta[b]pyridinyl group, 6,7-dihydro-5H-cyclopenta[c]pyridinyl group, 1,4,5,6-tetrahydrocyclopenta[c]pyrazolyl group, 2,4,5,6-tetrahydrocyclopenta[c]pyrazolyl group, 5,6-dihydro-4H-pyrrolo[1,2-b]pyrazolyl group, 6,7-dihydro-5H-pyrrolo[1,2-b][1,2,4]triazolyl group, 5,6,7,8-tetrahydro-[1,2,4]triazolo[1,2-a]pyridinyl group, 4,5,6,7-tetrahydropyrazolo[1,5-a]pyridinyl group, 4,5,6,7-tetrahydro-1H-indazolyl group, and 4,5,6,7-tetrahydro-2H-indazolyl group.

The term "heterocyclyl group" means a nonaromatic carbocyclic system containing one, two, three or four heteroatoms selected independently from oxygen, nitrogen, and sulfur and having one, two or three rings wherein such rings may be fused, wherein fused is defined above. Heterocyclyl group also includes bicyclic structures that may be bridged or spirocyclic in nature with each individual ring within the bicycle varying from 3-8 atoms, and containing 0, 1, or 2 N, O or S atoms. The term "heterocyclyl group" Includes but is not limited to lactones, lactams, cyclic ethers and cyclic amines, including the following exemplary ring systems: pyrrolidinonyl group, 2,5-dihydro-1H-pyrrolyl group, piperidinonyl group, morpholinonyl group, piperazinonyl group, oxazolidinonyl group, imidazolidinonyl group, 1,3-oxazinan-2-onyl group, epoxidyl group, tetrahydrofuranyl group, tetrahydropyranyl group, dioxanyl group, aziridinyl group, azetidinyl group, oxetanyl group, pyrrolidinyl group, oxazolidinyl group, thiazolidinyl group, piperidinyl group, morpholinyl group, piperazinyl group, thiomorpholinyl group, 1,3-oxazinanyl group, 1,3-thiazinanyl group, 2-azabicyclo[2,1,1]hexanyl group, 5-azabicyclo[2,1,1]hexanyl group, 6-azabicyclo[3,1,1]heptanyl group, 2-azabicyclo[2,2,1]heptanyl group, 3-azabicyclo[3,1,0]hexanyl group, 2-azabicyclo[3,1,0]hexanyl group, 3-azabicyclo[3,2,1]octanyl group, 8-azabicyclo[3,2,1]octanyl group, 3-oxa-7-azabicyclo[3,3,1]nonanyl group, 3-oxa-9-azabicyclo[3,3,1]nonanyl group, 2-oxa-5-azabicyclo[2,2,1]heptanyl group, 6-oxa-3-azabicyclo[3,1,1]heptanyl group, 2-azaspiro[3,3]heptanyl group, and 2-oxa-6-azaspiro[3,3]heptanyl group.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form).

As used herein, the expressions "reaction-inert solvent" and "inert solvent" refer to a solvent or a mixture thereof which does not interact with starting materials, reagents, intermediates or products in a manner which adversely affects the yield of the desired product.

In an embodiment of the present invention, a sulfoxide compound of formula (I) is provided, wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain; X is halogen atom. In one embodiment, the sulfoxide compound can be synthesized by the reaction as Reaction Scheme 2 shown below. In an example of the sulfoxide compound, $R_1$ and $R_2$ are both methyl group, and X is bromine atom.

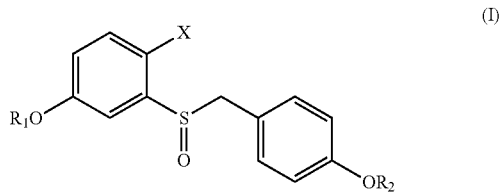

(I)

[Reaction Scheme 2]

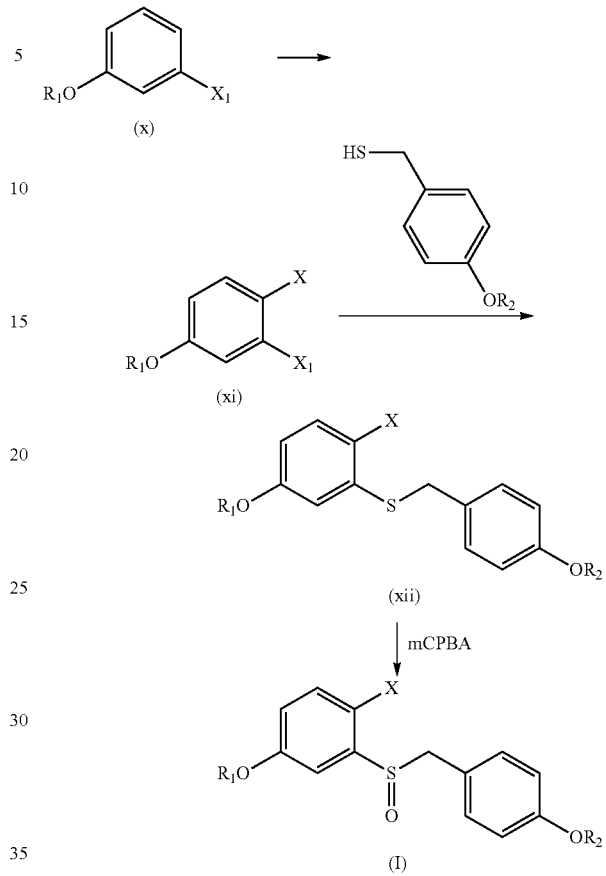

In Reaction Scheme 2, $R_1$, $R_2$ and X are defined as above, and $X_1$ is a different halogen atom from X. First, 3-halide-anisole [e.g. compound of formula (x)], such as 3-iodoanisole, reacts with N-bromosuccinimide (NBS), for example, to replace the hydrogen atom on para-site of 3-iodoanisole with bromine atom. Then, C—S (carbon-sulfur) bond formation reaction is performed, using 4-alkoxybenzyl mercaptan to substitute $X_1$ of compound (xi), to form the sulfide compound of formula (xii). It is noted that $X_1$ is a halogen atom selected to be a better leaving group than X, for example, $X_1$ is iodine atom, while X is bromine atom. Use meta-chloroperoxybenzoic acid (mCPBA) to oxidize sulfide compound of formula (xii), and the sulfoxide compound of formula (I) is then produced.

In another embodiment of the present invention, a method of producing benzothiophene derivatives is provided. The method comprises performing a reaction using the sulfoxide compound of formula (I) and an alkynyl compound. The alkynyl compound has a structure of formula (II) shown below, wherein A can be hydrogen atom or silyl group, and $R_4$ is benzoyl group; alkyl, acyl or silyl group of $C_1$-$C_6$ straight chain or branched chain; or alkenyl group of $C_3$-$C_6$ straight chain or branched chain. The produced benzothiophene derivatives have formula (III) shown below, wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain, and $R_3$ is hydrogen atom or (1-piperidinyl)-($C_1$-$C_4$)alkyl group.

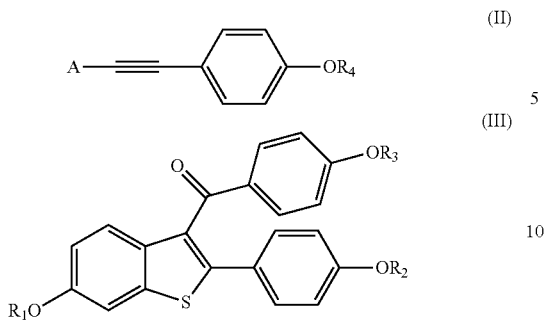

(II)

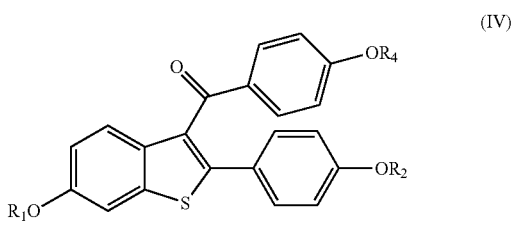

(III)

In an embodiment of the present invention, the reaction between the sulfoxide compound of formula (I) and the alkynyl compound of formula (II) is performed for more than 24 hours, and it is preferably performed for 24 hours to 72 hours. A one-pot reaction is performed under Sonogashira coupling reaction condition, that is, palladium catalyst is used. The first intermediate of formula (IV) is produced, wherein $R_1$, $R_2$ and $R_4$ are individually and independently benzoyl group; alkyl, acyl or silyl group of $C_1$-$C_6$ straight chain or branched chain; or alkenyl group of $C_3$-$C_6$ straight chain or branched chain.

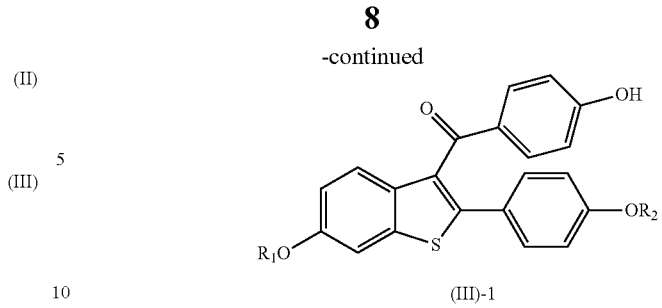

(IV)

The selective substitution reaction of the first intermediate [formula (IV)], which replaces the substituent $R_4$ to the substituent $R_3$, for example, hydrogen atom, can be performed. In an example, as shown in Reaction Scheme 3, the first intermediate transforms to benzothiophene derivatives of formula (III), wherein $R_3$ is hydrogen atom, which refers to as formula (III)-1. For example, the selective demethylation reaction is performed between the first Intermediate and sodium ethanethiolate, while the substituent $R_4$ is methyl group, the benzothiophene derivatives of formula (III)-1 is then produced. Using lithium hydroxide or sodium hydroxide, while the substituent $R_4$ is acetyl group, can make the first intermediate react to the benzothiophene derivatives of formula (III)-1, too. The same reaction can also occur by using tetra-n-butylammonium fluoride (TBAF) or calcium carbonate and methanol while the substituent $R_4$ is silyl group.

[Reaction Scheme 3]

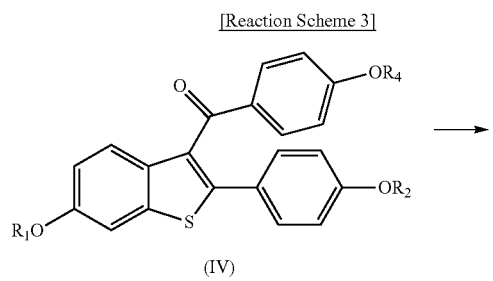

-continued

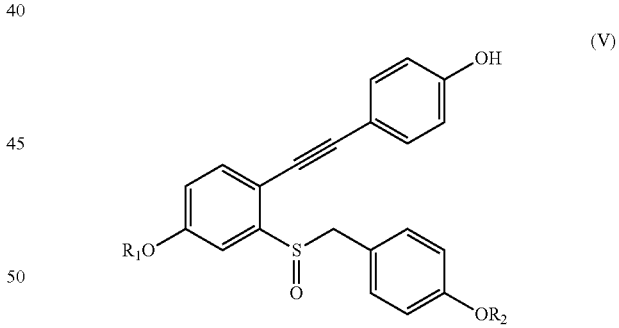

(III)-1

In another embodiment of the present invention, the reaction time between the sulfoxide compound of formula (I) and the alkynyl compound of formula (II) reduces to less than 24 hour, which preferably for about 6 hours to about 24 hours. Before the benzothiophene derivatives of formula (III) is produced, the second intermediate of formula (V) can be produced first, wherein $R_1$ and $R_2$ are individually and independently hydrogen atom, benzoyl group; alkyl, acyl, or silyl group of $C_1$-$C_5$ straight chain or branched chain; or alkenyl group of $C_3$-$C_6$ straight chain or branched chain. The intramolecular cyclization of the second intermediate is conducted to form the benzothiophene derivatives of formula (III)-1. The intramolecular cyclization is occurred by adding the certain catalyst. In an embodiment, the catalyst is a composition comprising mercury, such as mercury chloride ($HgCl_2$), mercury oxide (HgO), and mercury acetate [$Hg(OAc)_2$], and mercury chloride is preferable. In another embodiment, in addition to the presence of the catalyst, adding the oxidant such as 2,3-dichloro-5,6-dicyano-1,4-benzoquinone (DDQ) can further increase the yield. In an embodiment, the reaction inert solvent is selected from benzene, dichloromethane, 1,4-dioxane or 1,2-dichloroethane (DCE), and benzene as solvent shows better effect. Moreover, the reaction is preferably performed by refluxing in the inert solvent.

(V)

Under the both reaction conditions discussed above, after forming the benzothiophene derivatives of formula (III)-1, raloxifene can be produced by the reaction shown in Reaction Scheme 4, for example. First, the benzothiophene derivatives of formula (III)-1 is reacted with 1-(2-haloethyl) piperidine of formula (VI) to produce the benzothiophene derivatives of formula (VII), wherein $R_1$ and $R_2$ are individually and independently benzoyl group; alkyl, acyl or silyl group of $C_1$-$C_6$ straight chain or branched chain; or alkenyl group of $C_3$-$C_6$ straight chain or branched chain. Thereafter, the substituents $R_1$ and $R_2$ are replaced by hydrogen atom, and then raloxifene of formula (VII)-1 can be produced.

[Reaction Scheme 4]

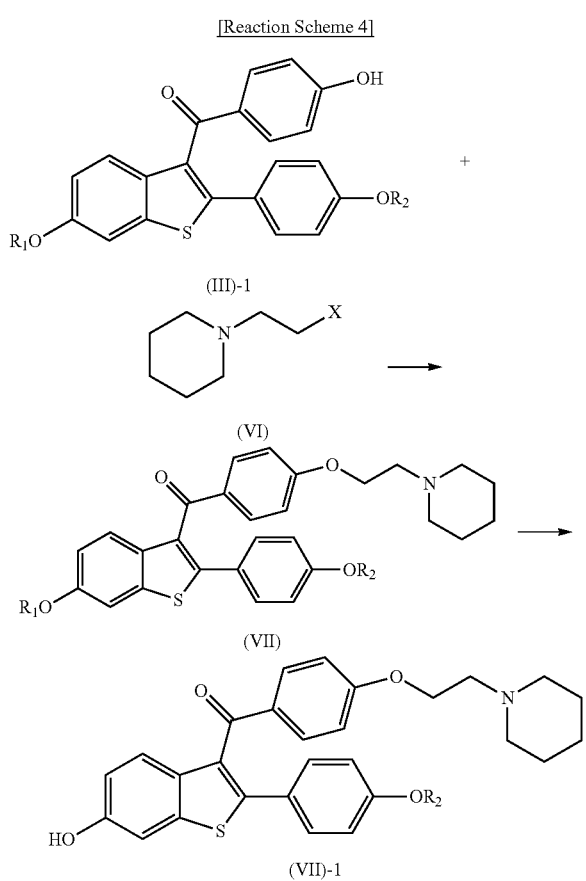

The following Embodiments are provided to better elucidate the practice of the present invention and should not be interpreted in anyway as to limit the scope of same. Those skilled in the art will recognize that various modifications may be made while not departing from the spirit and scope of the invention. All publication and patent applications mentioned in the specification are indicative of the level of those skilled in the art to which this invention pertains.

Embodiment 1: Formation of 2-bromo-6-methoxyphenyl-4-methoxybenzyl

Step A: Synthesis of 4-bromo-3-iodoanisole

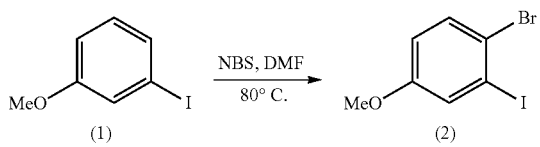 [SMILES: COc1cccc(I)c1 ; COc1ccc(Br)c(I)c1]

2.0 g 3-iodoanisole [formula (1)] was dissolved in dimethylforamide (DMF) (20 mL), and was added 1.54 g N-bromosuccinimide (NBS). The reaction mixture was heated to 80° C. and stirred at this temperature for 6 hours. After cooling to room temperature, the mixture was quenched with the saturated aqueous NaCl solution (100 mL), 6N aqueous solution of HCl (10 mL), and extracted with ethyl acetate (EtOAc) (50 mL×3). The combined organic extracts were dried over anhydrous magnesium sulfate ($MgSO_4$). After filtration and removal of solvent, the residue was purified by column chromatography on silica using 20/1 (Hexane/EtOAc) as eluent to obtain a product, 2.4 g 4-bromo-3-iodoanisole [formula (2)] and the yield was 90%. The results obtained were as follows:

Rf=0.65 (20:1 Hexane/EtOAc)

$^1$H NMR: (500 MHz, $CDCl_3$) δ 3.75 (s, 3H), 6.74 (dd, J=9.0, 3.0 Hz, 1H), 7.36 (d, J=3.0 Hz, 1H), 7.44 (d, J=9.0 Hz, 1H)

$^{13}$C NMR (125 MHz, $CDCl_3$): δ 55.6, 101.0, 115.9, 120.1, 125.3, 132.5, 158.6

MS: (EI, m/z) 314 ($M^+$+2, 100), 312 ($M^+$, 100), 297 (14), 269 (12), 185 (12), 170 (21), 78 (16), 63 (33)

HRMS: m/z calculated for $C_7H_6BrIO$ 311.8647. found 311.8646.

Step B: Synthesis of 4-bromo-3-(4-methoxybenzylmercapto) anisole

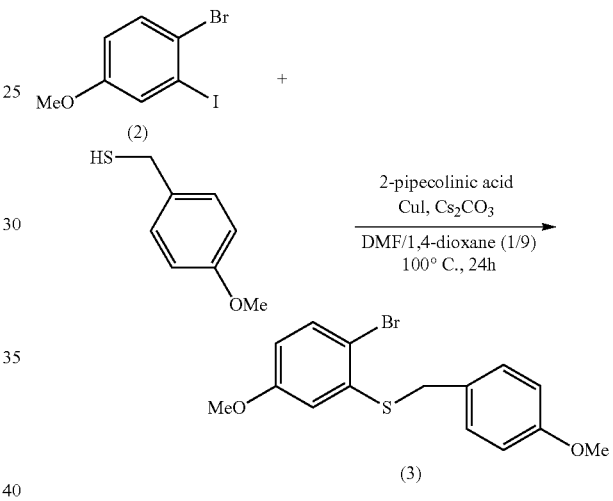

0.183 g cuprous iodide (CuI), 0.124 g DL-pipecolinic acid and 4.18 g cesium carbonate ($Cs_2CO_3$) were dissolved in 50 mL of DMF/1,4-dioxane (1/9), and was added 1.07 ml 4-methoxybenzyl mercaptan. Then, the reaction mixture was stirred at room temperature for 3 minutes. 2.0 g 4-Bromo-3-Iodoanisole [formula (2)], which was synthesized by step A, was then added into the mixture, and the resulting solution was heated to 100° C. and stirred at this temperature for 24 hours. After cooling to room temperature, the mixture was filtrated through celite and washed with EtOAc (20 mL). Then, the organic layer was added saturated aqueous NaCl solution (100 mL) and was extracted with EtOAc (50 mL×3). The combined organic extracts were dried over anhydrous $MgSO_4$. After filtration and removal of solvent, the residue was purified by column chromatography on silica gel using 10/1 (Hexane/EtOAc) as eluent to obtain a compound, 1.60 g 4-bromo-3-(4-methoxybenzylmercapto) anisole [formula (3)], and the yield was 75%. The results obtained were as follows:

Rf=0.30 (10:1 Hexane/EtOAc)

$^1$H NMR (500 MHz, $CDCl_3$): δ 3.72 (s, 3H), 3.79 (s, 3H), 4.10 (a, 2H), 6.58 (dd, J=9.0, 3.0 Hz, 1H), 6.78 (d, J=3.0 Hz, 1H), 6.85 (d, J=9.0 Hz, 2H), 7.29 (d, J=9.0 Hz, 2H), 7.41 (d, J=9.0 Hz, 1H)

$^{13}$C NMR (125 MHz, $CDCl_3$): δ 37.3, 55.2, 55.4, 112.3, 113.6, 113.9, 114.4, 127.8, 130.0, 133.2, 138.9, 158.9, 159.0

MS: (EI, m/z) 340 (M$^+$, 7), 338 (6), 138 (7), 121 (100), 71 (8), 57 (8) HRMS: m/z calculated for $C_{15}H_{15}BrO_2S$ 339.9956. found 339.9979.

Step C: Synthesis of 2-bromo-5-methoxyphenyl-4-methoxybenzyl sulfoxide

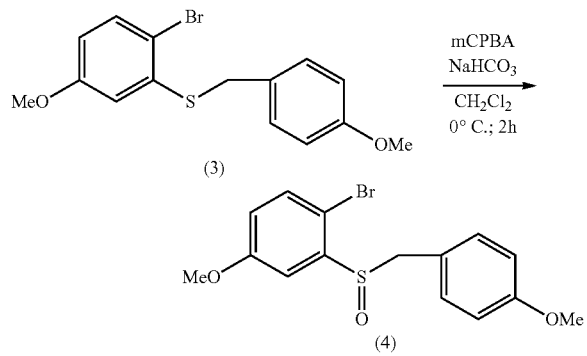

1.60 g 4-bromo-3-(4-methoxybenzylmercapto) anisole [formula (3)], which is synthesized by step B, was dissolved in dichloromethane (40 mL), and was added 0.817 g meta-chloroperoxybenzoic acid (mCPBA) and 0.395 g sodium bicarbonate (NaHCO$_3$). The reaction mixture was stirred in ice bath for 2 hours and quenched with 100 mL saturated aqueous sodium thiosulfate (Na$_2$S$_2$O$_3$) solution and extracted with dichloromethane (30 mL×3). The combined organic extracts were dried over anhydrous MgSO$_4$. After filtration and removal of solvent, the residue was purified by column chromatography on silica gel using 1/1 (Hexane/EtOAc) as eluent to obtain a product, 1.35 g 2-bromo-5-methoxyphenyl-4-methoxybenzyl sulfoxide [formula (4)], and the yield was 81%. The results obtained were as follows:

Rf=0.65 (1:1 Hex/EtOAc)

$^1$H NMR (500 MHz, CDCl$_3$): δ 3.66 (s, 3H), 3.77 (s, 3H), 3.95 (d, J=13.5 Hz, 1H), 4.24 (d, J=13.5 Hz, 1H), 6.78 (d, J=8.5 Hz, 2H), 6.84 (dd, J=8.5, 3.0 Hz, 1H), 8.90 (d, J=3.0 Hz, 1H), 6.97 (d, J=8.5 Hz, 2H), 7.40 (d, J=8.5 Hz, 1H)

$^{13}$C NMR (125 MHz, CDCl$_3$): δ 55.2, 55.6, 58.9, 108.5, 110.8, 113.6, 119.8, 121.1, 131.6, 133.3, 143.1, 159.6, 159.7

MS (EI, m/z): 235 (7), 233 (7), 121 (100), 106 (4), 91 (11), 78 (19), 77 (15)

HRMS: m/z calculated for $C_{15}H_{15}BrO_3S$ 355.9905. found 355.9927.

Embodiment 2: Formation of 4-tert-butyldimethylsiloxyphenyl trimethylsilyl acetylene

Step A: Synthesis of 4-iodophenyl tert-butyldimethylsilyl ether

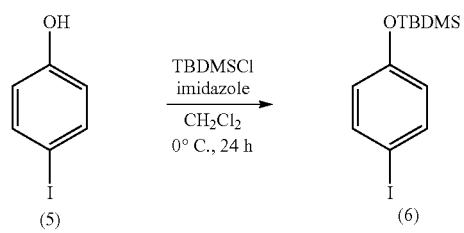 [SMILES: Oc1ccc(I)cc1 ; CC(C)(C)[Si](C)(C)Oc1ccc(I)cc1]

2.0 g 4-iodophenol [formula (5)] was dissolved in dichloromethane (50 mL). Until the solution was cooled to 0° C., it was added 60 g tert-butyldimethylsilyl chloride (TBDMSCl) followed by 0.68 g imidazole. The reaction mixture was stirred for 30 minutes at 0° C. then warmed to room temperature and stirred for another 24 hours. During which time a white solid precipitated and that was removed by filtration. The filtrate was concentrated under vacuum, and the residue was purified by column chromatography on silica using Hexane as eluent to obtain a compound, 2.90 g 4-iodophenyl tert-butyldimethylsilyl ether [formula (6)], and the yield was 98%. The results obtained were as follows:

Rf=0.65 (Hexane)

$^1$H NMR (500 MHz, CDCl$_3$): δ 0.21 (s, 6H), 0.99 (s, 9H), 6.63 (d, J=9.0 Hz, 2H), 7.52 (d, J=9.0 Hz, 2H)

$^{13}$C NMR (125 MHz, CDCl$_3$): δ −4.5, 18.2, 25.6, 83.7, 122.5, 138.3, 155.6

MS (EI, m/z): 334 (M$^+$, 34), 277 (100), 150 (68), 279 (6), 135 (27)

HRMS: m/z calculated for $C_{12}H_{19}ISOi$ 334.0250. found 334.0252.

Step B: Synthesis of 4-tert-butyldimethylsiloxyphenyl trimethylsilyl acetylene

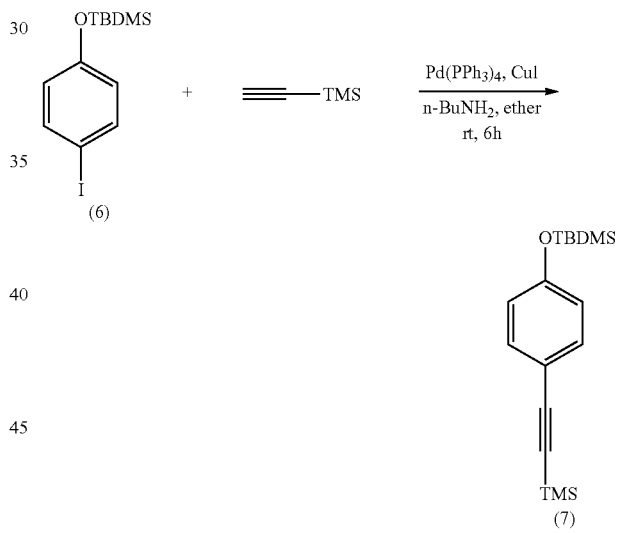

2.0 g 4-iodophenyl tert-butyldimethylsilyl ether [formula (6)], which was synthesized by step A, was dissolved in ethyl ether (50 mL), and was added 0.35 g tetrakis(triphenylphosphine)palladium [Pd(PPh$_3$)$_4$]. After stirring for 3 minutes, 0.11 g CuI, 1.28 mL trimethylsilylacetylene and 2.0 mL n-butylamine were added into the solution. The reaction mixture was stirred at room temperature for 6 hours. The reaction mixture was quenched with saturated aqueous NH$_4$Cl solution (100 mL) and extracted with EtOAc (50 mL×3). The combined organic extracts were dried over anhydrous MgSO$_4$. After filtration and removal of solvent, the residue was purified by column chromatography on silica using 10/1 (Hexane/EtOAc) as eluent to obtain a compound, 1.67 g 4-tert-butyldimethylsiloxyphenyl trimethylsilyl acetylene [formula (7)], and the yield was 92%. The results obtained were as follows:

Rf=0.50 (Hexane)

¹H NMR (500 MHz, CDCl₃): δ 0.19 (s, 6H), 0.25 (s, 9H), 0.98 (s, 9H), 6.76 (d, J=9.0 Hz, 2H), 7.36 (d, J=9.0 Hz, 2H)

¹³C NMR (125 MHz, CDCl₃): δ −4.5, 0.1, 18.2, 25.6, 92.6, 105.2, 115.9, 120.1, 133.4, 156.1

MS (EI, m/z): 304 (M⁺, 27), 247 (100), 116 (13), 73 (34)

HRMS: m/z calculated for C₁₇H₂₈OSi₂ 304.1679. found 304.1679.

Embodiment 3: Formation of 2-(4-methoxyphenyl)-3-(4-hydroxybenzoyl)-6-methoxythiophene Step A: Synthesis of 2-[2-(4-hydroxyphenyl)ethynyl]-5-methoxyphenyl 4-methoxybenzyl sulfoxide

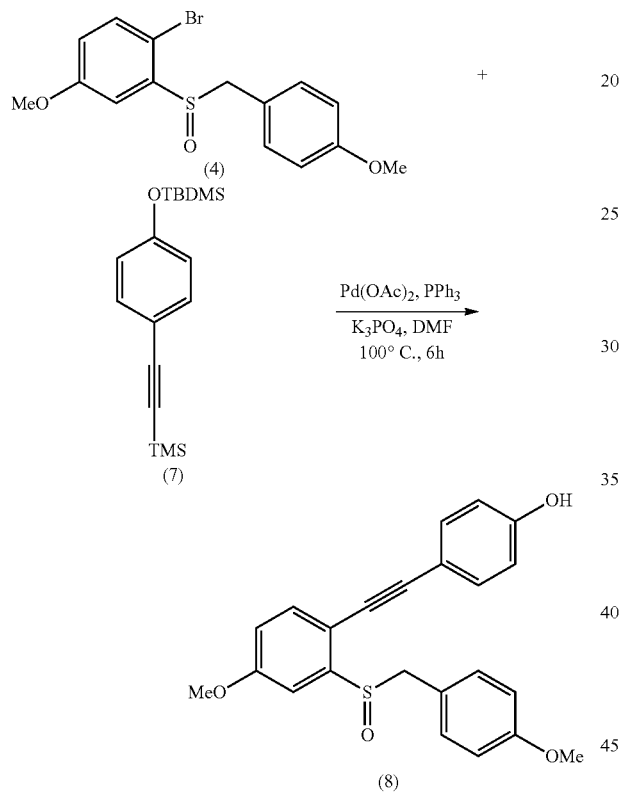

1.0 g 2-bromo-5-methoxyphenyl-4-methoxybenzyl sulfoxide [formula (4)], which was produced by the method of the embodiment 1, was dissolved in DMF (20 mL), and was added 75 mg palladium acetate [Pd(OAc)₂], 349 mg triphenylphosphine (PPh₃) and 2.0 g potassium phosphate (K₃PO₄) subsequently. Then, the flask with the aforementioned mixture was evacuated and backfilled with nitrogen and the mixture was stirred at room temperature for 3 minutes. 1.5 g 4-tert-butyldimethylsiloxyphenyl trimethylsilyl acetylene [formula (7)] was then added into the reaction mixture. The reaction mixture was heated to 100° C. and stirred at this temperature for 6 hours. After cooling to room temperature, the mixture was quenched with the saturated aqueous NaCl solution (50 mL), 6N aqueous solution of HCl (10 mL) and extracted with EtOAc (40 mL×3). The combined organic extracts were dried over anhydrous MgSO₄. After filtration and removal of solvent, the residue was purified by column chromatography on silica gel using 1/1 (Hexane/EtOAc) as eluent to obtain a product, 775 mg 2-[2-(4-hydroxyphenyl)ethynyl]-5-methoxyphenyl 4-methoxybenzyl sulfoxide [formula (8)], and the yield was 70%. The results obtained were as follows:

m.p.: 159° C.-161° C.

Rf=0.40 (1:1 Hex/EtOAc)

¹H NMR (500 MHz, CDCl₃): δ 3.75 (d, J=4.0 Hz, 6H), 4.00 (d, J=13.0 Hz, 1H), 4.33 (d, J=13.0 Hz, 1H), 6.10 (s, 1H), 6.75 (d, J=9.0 Hz, 2H), 6.85 (d, J a 8.5 Hz, 2H), 6.94 (dd, J=8.5, 2.5 Hz, 1H), 6.98 (d, J=8.5 Hz, 2H), 7.06 (d, J=2.5 Hz, 1H), 7.41 (d, J=8.5 Hz, 2H), 7.46 (d, J=8.5 Hz, 1H)

¹³C NMR (125 MHz, CDCl₃): δ 55.3, 55.7, 60.0, 83.0, 96.8, 108.5, 111.9, 113.8, 114.3, 115.8, 117.9, 121.6, 131.7, 133.1, 133.3, 145.6, 156.7, 159.7, 160.2

MS (EI, m/z): 394 (M⁺+2, 1), 257 (11), 111 (21), 97 (38), 85 (64), 57 (100)

HRMS: m/z calculated for C₂₃H₂₀O₄S 392.1082. found 392.1082.

Step B: Synthesis of 2-(4-methoxyphenyl)-3-(4-hydroxybenzoyl)-6-methoxythiophene

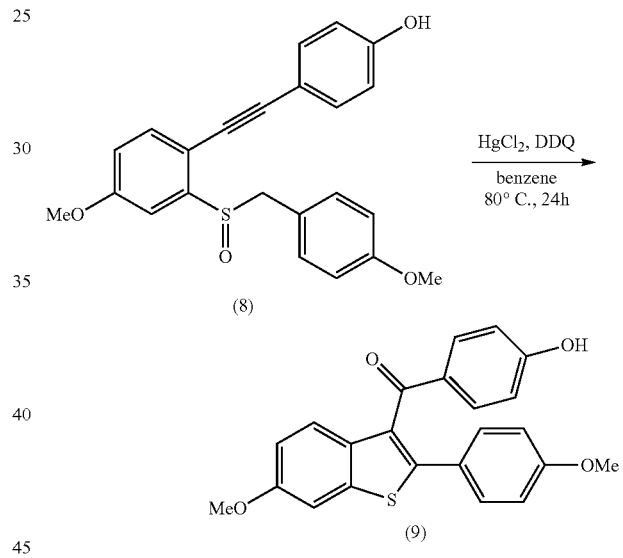

0.78 g 2-[2-(4-hydroxyphenyl)ethynyl]-5-methoxyphenyl 4-methoxybenzyl sulfoxide [formula (8)], which was synthesized by step A, was dissolved in benzene (20 mL), and was added 53.6 mg HgCl₂ and 0.45 g 2,3-Dichloro-5,6-dicyano-1,4-benzoquinone (DDQ). The reaction mixture was heated to refluxing temperature and stirred for 24 hours. After cooling to room temperature, the reaction mixture was filtrated through celite and washed with EtOAc (30 mL). The organic solvent was then removed in vacuum and the residue was purified by column chromatography on silica gel using 1/1 (Hexane/EtOAc) as eluent to obtain a product, 0.65 g 2-(4-methoxyphenyl)-3-(4-hydroxybenzoyl)-6-methoxythiophene [formula (9)], and the yield was 84%. The results obtained were as follows:

Rf=0.55 (1:1 Hex/EtOAc)

¹H NMR (500 MHz, CDCl₃): δ 3.74 (s, 3H), 3.88 (s, 3H), 6.41 (brs, OH), 6.67 (d, J=9.0, 2.0 Hz, 1H), 7.32 (s, 1H), 7.33 (d, J=8.5 Hz, 2H), 7.51 (d, J=9.0 Hz, 1H), 7.70 (d, J=8.5 Hz, 2H)

¹³C NMR (125 MHz, CDCl₃): δ 55.2, 55.6, 104.5, 114.1, 114.8, 115.3, 124.0, 125.9, 130.2, 130.3, 130.4, 132.7, 133.9, 140.0, 142.9, 157.6, 159.7, 160.7, 193.6 MS (EI, m/z): 390 (M⁺, 12), 85 (69), 71 (98), 57 (100)

HRMS: m/z calculated for $C_{23}H_{18}O_4S$ 390.0926. found 390.0925.

Embodiment 4: Formation of 2-(4-methoxyphenyl)-3-(4-methoxybenzoyl)-6-methoxybenzothiophene

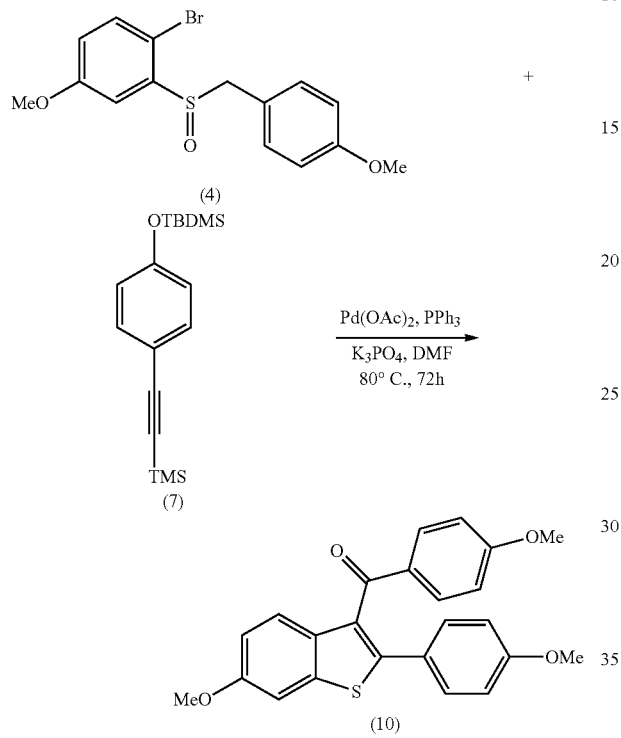

0.50 g 2-bromo-5-methoxyphenyl-4-methoxybenzyl sulfoxide [formula (4)], which was produced by the method of the embodiment 1, was dissolved in DMF (10 mL), and was added 60 mg Pd(OAc)$_2$, 0.15 g PPh$_3$ and 0.36 g K$_3$PO$_4$ subsequently. Then, the flask was evacuated and backfilled with nitrogen and the mixture was stirred at room temperature for 3 minutes. 0.28 g 4-tert-butyldimethylsiloxyphenyl trimethylsilyl acetylene [formula (7)] was then added into the reaction mixture. The reaction mixture was heated to 80° C. and stirred at this temperature for 72 hours. After cooling to room temperature, the mixture was quenched with the saturated aqueous NaCl solution (30 mL), 6N aqueous solution of HCl (10 mL) and extracted with EtOAc (20 mL×3). The combined organic extracts were dried over anhydrous MgSO$_4$. After filtration and removal of solvent, the residue was purified by column chromatography on silica gel using 5/1 (Hexane/EtOAc) as eluent to obtain a product, 0.31 g 2-(4-methoxyphenyl)-3-(4-methoxybenzoyl)-6-methoxybenzothiophene [formula (10)], and the yield was 54%. The results obtained were as follows:
Rf=0.80 (2:1 Hexane/EtOAc)

¹H NMR (500 MHz, CDCl$_3$): δ 3.75 (s, 3H), 3.80 (s, 3H), 3.89 (s, 3H), 6.76 (dd, J=9.0, 3.0 Hz, 4H), 6.96 (dd, J=9.0, 2.5 Hz, 1H), 7.32 (d, J=2.5 Hz, 1H), 7.35 (d, J=9.0 Hz, 2H), 7.52 (d, J=9.0 Hz, 1H), 7.78 (d, J=8.5 Hz, 2H)

¹³C NMR (125 MHz, CDCl$_3$): δ 55.2, 55.4, 55.6, 104.5, 113.6, 114.0, 114.7, 124.0, 126.0, 130.2, 130.4, 130.5, 132.3, 134.0, 140.0, 142.4, 157.6, 159.7, 163.7, 193.2

MS (EI, m/z): 404 (M⁺, 69), 389 (18), 308 (29), 251 (68), 236 (31), 135 (100), 85 (78), 71 (81), 57 (79)

HRMS: m/z calculated for $C_{24}H_{20}O_4S$ 404.1082. found 404.1082.

Embodiment 5: Formation of Raloxifene

Step A: Synthesis of 2-(4-methoxyphenyl)-3-[4-(2-piperidinylethoxy)benzoyl]-6-methoxythiophene

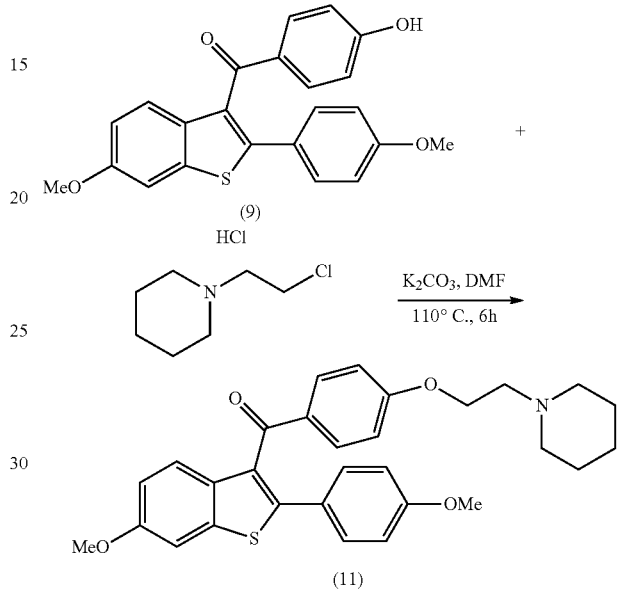

0.65 g 2-(4-methoxyphenyl)-3-(4-hydroxybenzoyl)-6-methoxythiophene [formula (9)], which was produced by the method of the embodiment 3, was dissolved in DMF (20 mL), and was added 0.37 g 1-(2-chloroethyl)piperidine hydrogen chloride salt and 0.55 g potassium carbonate. The reaction mixture was heated to 110° C. and stirred at this temperature for 6 hours. After cooling to room temperature, the mixture was quenched with the saturated aqueous ammonium chloride (NH$_4$Cl) solution (100 mL) and extracted with EtOAc (30 mL×3). The combined organic extracts were dried over anhydrous MgSO$_4$. After filtration and removal of solvent, the residue was purified by column chromatography on silica gel using 10/1 (dichloromethane/methanol) as eluent to obtain a compound, 0.69 g 2-(4-methoxyphenyl)-3-[4-(2-piperidinylethoxy) benzoyl]-6-methoxythiophene [formula (11)], and the yield was 83%. The results obtained were as follows:
Rf=0.45 (10:1 Dichloromethane/MeOH)

¹H NMR (500 MHz, CDCl$_3$): δ 1.44 (d, J=5.5 Hz, 2H), 1.57-1.62 (m, 4H), 2.48 (s, 4H), 2.74 (t, J=6.0 Hz, 2H), 3.75 (s, 3H), 3.88 (s, 3H), 4.09 (t, J=6.0 Hz, 2H), 6.76 (dd, J=9.0, 3.0 Hz, 4H), 6.95 (dd, J=9.0, 2.5 Hz, 1H), 7.31 (d, J=8.5 Hz, 1H), 7.34 (d, J=9.0 Hz, 2H), 7.51 (d, J=8.5 Hz, 1H), 7.75 (d, J=9.0 Hz, 2H)

¹³C NMR (125 MHz, CDCl$_3$): δ 24.1, 25.8, 55.0, 55.2, 55.6, 57.6, 66.1, 104.5, 114.0, 114.2, 114.7, 124.0, 125.9, 130.2, 130.4, 130.5, 132.3, 133.9, 140.0, 142.4, 157.6, 159.7, 162.9, 193.2

MS (EI, m/z): 501 (M⁺, 5), 98 (100), 71 (89), 57 (86)

HRMS: m/z calculated for $C_{30}H_{31}NO_4S$ 501.1974. found 501.1976.

Step B: Synthesis of Raloxifene

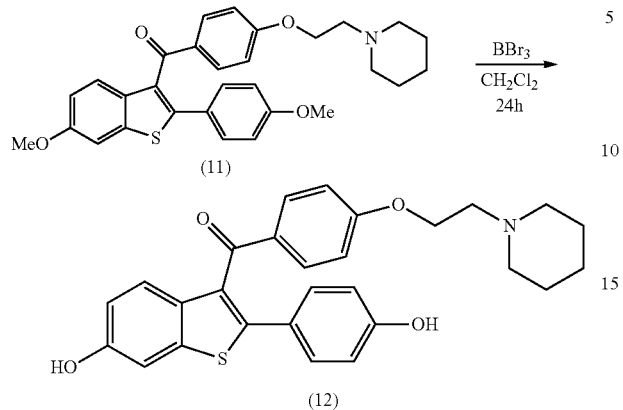

0.69 g 2-(4-methoxyphenyl)-3-[4-(2-piperidinylethoxy)benzoyl]-6-methoxythiophene [formula (11)], which was synthesized by step A, was dissolved in dried dichloromethane (40 mL), and was added 12 mL boron tribromide (BBr$_3$) (1 M solution in dichloromethane) slowly at 0° C. After stirring at 0° C. for 30 minutes, the reaction mixture was allowed to warm to room temperature and stirred for another 24 hours. The saturated aqueous NaHCO$_3$ solution was added slowly into the reaction mixture, and the pH value of the solution was controlled at 7.0. After stirring for 30 minutes, the reaction mixture was added saturated aqueous NaCl solution (100 mL) and extracted with EtOAc (40 mL×3). The combined organic extracts were dried over anhydrous MgSO$_4$. After filtration and removal of solvent, the residue was purified by column chromatography on silica gel using 10/1 (dichloromethane/methanol) as eluent to obtain a 0.39 g raloxifene [formula (12)], and the yield was 60%. The results obtained were as follows:

m.p. 120-125° C.

Rf=0.23 (10:1 Dichloromethane/MeOH)

$^1$H NMR (500 MHz, DMSO-d$_6$): δ 1.33 (d, J=5.0 Hz, 2H), 1.45 (t, J=8.0 Hz, 4H), 2.40 (s, 4H), 2.62 (t, J=5.5 Hz, 2H), 4.06 (t, J=5.5 Hz, 2H), 6.68 (d, J=8.5 Hz, 2H), 6.86 (dd, J=9.0, 2.0 Hz, 1H), 6.89 (d, J=9.0 Hz, 2H), 7.18 (d, J=9.0 Hz, 2H), 7.26 (d, J=8.5 Hz, 1H), 7.35 (d, J=2.0 Hz, 1H), 7.65 (d, J=8.5 Hz, 2H), 9.82 (br, 20H)

$^{13}$C NMR (125 MHz, DMSO-d$_6$): δ 23.8, 25.4, 54.3, 57.0, 65.8, 107.2, 114.5, 115.2, 115.7, 123.4, 123.8, 129.73, 129.75, 131.8, 132.3, 139.3, 140.4, 155.5, 157.9, 162.8, 192.6

MS (EI, m/z): 475 (M$^+$2, 31), 474 (M$^+$+1, 100)

HRMS: m/z calculated for C$_{28}$H$_{27}$NO$_4$S 474.1734. found 474.1731.

According to various embodiments discussed above, the sulfoxide compound and the alkynyl compound can be formed by using such methods of the embodiments shown above, then perform a reaction between the both compounds. The benzothiophene derivatives, such as raloxifene, can be produced by simple process with relatively high yield.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the Invention. In view of the foregoing, it is intended that the present invention cover modifications and variations of this invention provided they fall within the scope of the following claims.

What is claimed is:

1. A method of producing benzothiophene derivatives, comprising:
performing a reaction between a sulfoxide compound of formula (I) and an alkynyl compound of formula (II) to produce the benzothiophene derivatives of formula (III):

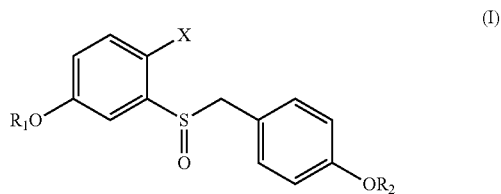

wherein R$_1$ and R$_2$ are individually and independently benzoyl group; alkyl, acyl or silyl group of C$_1$-C$_6$ straight chain or branched chain; or alkenyl group of C$_3$-C$_6$ straight chain or branched chain; and X is halogen atom;

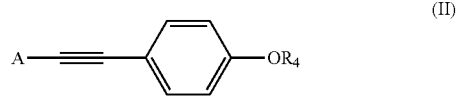

wherein in the formula (II), A is hydrogen atom or silyl group, and R$_4$ is benzoyl group; alkyl, acyl or silyl group of C$_1$-C$_6$ straight chain or branched chain; or alkenyl group of C$_3$-C$_6$ straight chain or branched chain; and

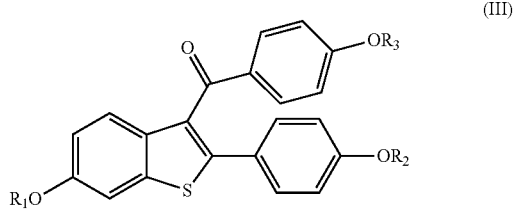

wherein in the formula (III), R$_1$ and R$_2$ are individually and independently hydrogen atom, benzoyl group; alkyl, acyl, or silyl group of C$_1$-C$_6$ straight chain or branched chain; or alkenyl group of C$_3$-C$_6$ straight chain or branched chain, and R$_3$ is hydrogen atom or (1-piperidinyl)-(C$_1$-C$_4$)alkyl group.

2. The method of claim 1, wherein the reaction further comprises:
reacting the sulfoxide compound and the alkynyl compound to form an intermediate, wherein the intermediate is a first intermediate or a second intermediate; and
forming the benzothiophene derivatives from the intermediate.

3. The method of claim 2, wherein the first intermediate has a structure of formula (IV):

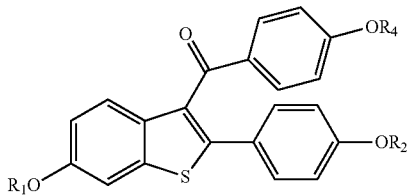

in the formula (IV), $R_1$, $R_2$ and $R_4$ are individually and independently hydrogen atom, benzoyl group; alkyl, acyl, or silyl group of $C_1$-$C_6$ straight chain or branched chain; or alkenyl group of $C_3$-$C_6$ straight chain or branched chain.

4. The method of claim 3, the reaction is performed for 24 hours to 72 hours.

5. The method of claim 2, wherein the second intermediate has a structure of formula (V):

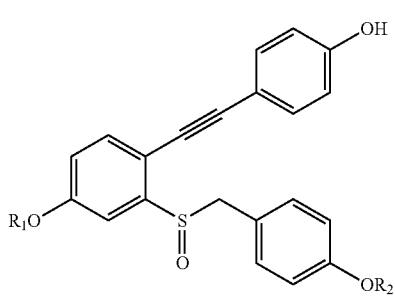

in the formula (V), wherein $R_1$ and $R_2$ are individually and independently hydrogen atom, benzoyl group; alkyl, acyl, or silyl group of $C_1$-$C_6$ straight chain or branched chain; or alkenyl group of $C_3$-$C_6$ straight chain or branched chain.

6. The method of claim 5, wherein the reaction is performed for 6 hours to 24 hours.

7. The method of claim 1, further comprising when the $R_3$ of the benzothiophene derivatives is hydrogen atom:
reacting the benzothiophene derivatives of formula (III) and a piperidine compound of formula (VI) to produce the benzothiophene derivatives of formula (VII):

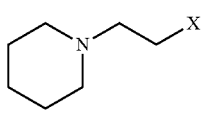

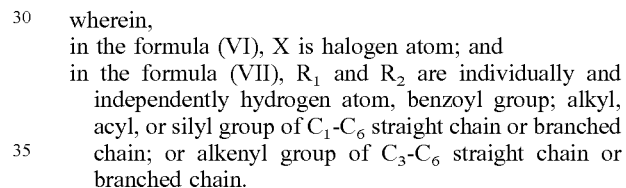

wherein,
in the formula (VI), X is halogen atom; and
in the formula (VII), $R_1$ and $R_2$ are individually and independently hydrogen atom, benzoyl group; alkyl, acyl, or silyl group of $C_1$-$C_6$ straight chain or branched chain; or alkenyl group of $C_3$-$C_6$ straight chain or branched chain.

* * * * *